United States Patent
Lindner

(10) Patent No.: US 9,482,580 B2
(45) Date of Patent: Nov. 1, 2016

(54) INSPECTION METHOD AND INSPECTION DEVICE FOR CONTAINERS

(71) Applicant: Peter Lindner, Neutraubling (DE)

(72) Inventor: Peter Lindner, Neutraubling (DE)

(73) Assignee: KRONES AG (DE)

( * ) Notice: Subject to any disclaimer, the term of this patent is extended or adjusted under 35 U.S.C. 154(b) by 0 days.

(21) Appl. No.: 14/647,831

(22) PCT Filed: Dec. 4, 2013

(86) PCT No.: PCT/EP2013/075583
§ 371 (c)(1),
(2) Date: May 28, 2015

(87) PCT Pub. No.: WO2014/086887
PCT Pub. Date: Jun. 12, 2014

(65) Prior Publication Data
US 2015/0308898 A1 Oct. 29, 2015

(30) Foreign Application Priority Data
Dec. 4, 2012 (DE) .................. 10 2012 111 770

(51) Int. Cl.
*G01J 5/02* (2006.01)
*G01N 25/72* (2006.01)
*B07C 5/34* (2006.01)
*G01J 5/10* (2006.01)
*G01N 21/90* (2006.01)
*G01J 5/00* (2006.01)

(52) U.S. Cl.
CPC ............ *G01J 5/0205* (2013.01); *B07C 5/3408* (2013.01); *G01J 5/10* (2013.01); *G01N 25/72* (2013.01); *G01J 2005/0077* (2013.01); *G01N 21/9072* (2013.01)

(58) Field of Classification Search
CPC .................... G01N 21/3581; G01N 25/72
See application file for complete search history.

(56) References Cited

U.S. PATENT DOCUMENTS

| 4,872,762 | A | | 10/1989 | Koshihara et al. |
| 5,259,716 | A | * | 11/1993 | Hoshino et al. ......... 414/223.01 |
| 2002/0063215 | A1 | * | 5/2002 | Yagita .......................... 250/341.1 |
| 2005/0087691 | A1 | * | 4/2005 | Cochran et al. ........... 250/341.1 |
| 2011/0094616 | A1 | * | 4/2011 | Hayakawa et al. ................ 141/1 |

FOREIGN PATENT DOCUMENTS

| DE | 3245908 A1 | 6/1984 |
| DE | 4302688 C1 | 8/1994 |

(Continued)

OTHER PUBLICATIONS

International Search Report; PCT/EP2013/075583; International Filing Date: Dec. 4, 2013; 3 pgs.

*Primary Examiner* — David Porta
*Assistant Examiner* — Hugh H Maupin
(74) *Attorney, Agent, or Firm* — Schmeiser, Olsen & Watts, LLP

(57) ABSTRACT

A method for inspecting drink containers, wherein the container is transported along a predefined transport path by means of a transport facility, and an outside wall of the container is tempered at least in sections, and wherein an area of the inside wall of the container is inspected through an orifice of the container during or after tempering of the outside wall by means of an inspection means is provided. The inspection means includes at least heat radiation emanating from the observed area of the inside wall, and conclusions are drawn from the recorded heat radiation as to the presence of foreign bodies between the observed area of the inside wall and the inspection means.

19 Claims, 1 Drawing Sheet

(56) References Cited

FOREIGN PATENT DOCUMENTS

Figure 1:
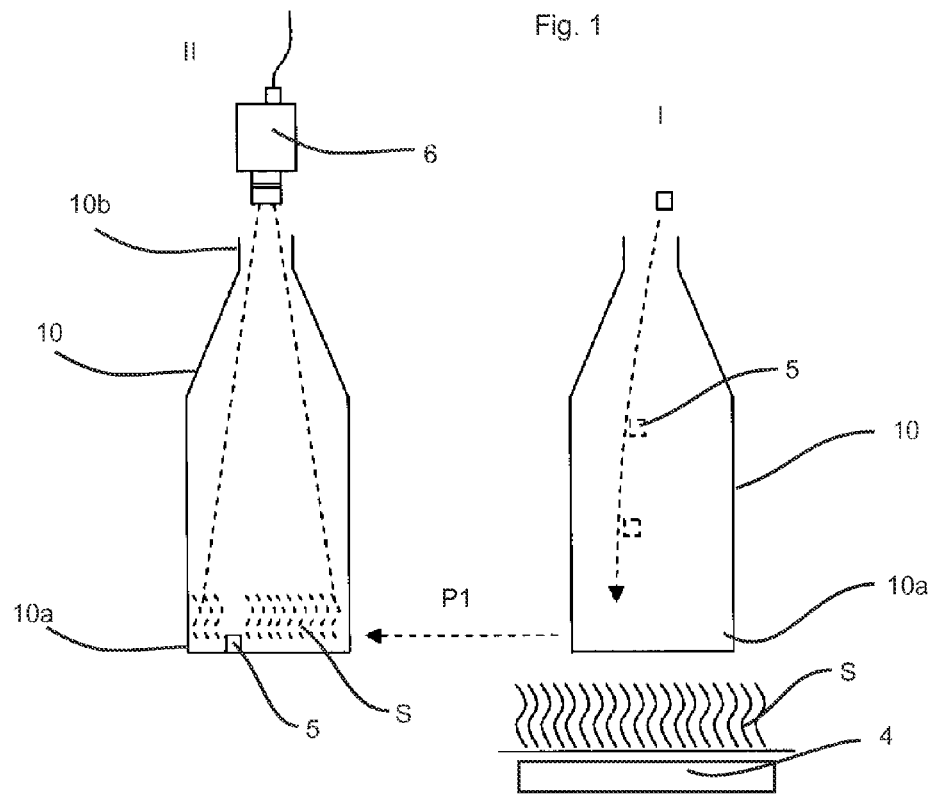

| | | |
|---|---|---|
| DE | 60037882 T2 | 1/2009 |
| EP | 0965836 A1 | 12/1999 |
| EP | 2442080 A1 | 4/2012 |
| JP | S5724811 A | 2/1982 |
| WO | WO00/66283 A1 | 11/2000 |
| WO | WO2012062449 A1 | 5/2012 |

* cited by examiner

U.S. Patent

Nov. 1, 2016

US 9,482,580 B2

INSPECTION METHOD AND INSPECTION DEVICE FOR CONTAINERS

CROSS-REFERENCE TO RELATED APPLICATIONS

This application claims priority to PCT Application No. PCT/EP2013/075583, having a filing date of Dec. 4, 2013, based on DE 10 2012 111 770.5, having a filing date of Dec. 4, 2012, the entire contents of which are hereby incorporated by reference.

FIELD OF TECHNOLOGY

The following relates to an inspection method and inspection device for containers.

BACKGROUND

A plurality of inspection methods for containers is known from the state of the art, in particular the drinks producing industry. As such it is known to inspect plastic containers for any defects during their manufacturing process. Furthermore methods and devices for checking the orifices of containers have been disclosed in the state of the art, which for example check whether orifices are faultless or whether glass breakages have occurred. A further criterion is the existence of foreign bodies in the containers, e.g. whether the containers contain pieces of broken glass. The inspection for such foreign bodies is often very difficult because the foreign bodies frequently consist of the same material as the container itself and are therefore very difficult to optically recognise. Also foreign bodies of this kind are very small and therefore difficult to detect. On the other hand, however, the existence of such foreign bodies in the containers may have far reaching consequences, for example if the consumer ingests these foreign bodies without being aware of them.

Therefore, devices and methods are known from the state of the art, with which containers are inspected with regard to such foreign bodies. As such the DE 600 37 882 T2 describes a device and a method for examining the structural integrity of liquid objects. This device comprises a sensor means and an electro-magnetic radiation source, wherein the sensor means functions so as to react to electro-magnetic radiation of one or more wavelengths or ranges of wavelengths. With this method the transparent container is illuminated from below, and the radiation passing through it is detected by the sensor device at the same time.

Embodiments of the present invention are based on the requirement to permit detection of foreign bodies in containers, in particular the occurrence of small foreign bodies. According to embodiments of the invention this requirement is met by the subjects of the independent claims. Advantageous embodiments and further developments are the subject of the sub-claims.

With a method according to embodiments of the invention for inspecting containers, in particular at least partially transparent containers, the container is transported by means of a transport facility along a predefined transport path with an outside wall of the container being tempered at least in sections, and furthermore an area of the inside wall of the container is inspected by means of an inspection means through the orifice of the container during or after tempering of the outside wall.

SUMMARY

According to embodiments of the invention the inspection device detects at least heat radiation emanating from the observed area of the inside wall and from the detected heat radiation conclusions are drawn as to the presence of foreign bodies between the observed area of the inside wall and the inspection device. In particular these foreign bodies are present in an optical path between the observed area and the inspection device and in particular these foreign bodies are present on a floor area inside the container.

It is therefore proposed in particular, to inspect the container by means of a thermal imaging camera/an inspection device taking thermal images. Preferably the container is a drinks container and in particular a bottle or a (drinking) glass or a drinking cup.

In particular the container may contain foreign bodies which lie inside the container, for example on the floor. Preferably therefore a floor inspection is carried out, wherein initially a defined area of the container such as e.g. a container floor is tempered and in particular heated, and subsequently the container floor is inspected through the orifice of the container by means of a thermal imaging camera. Due to the varying heat emission solids other than the material of the container may be depicted in the thermal image. When observing the especially critical area between the inspection device and the filling means, glass splinters for example created through glass breakage and therefore comprising a temperature different from the container floor, would be able to be directly detected in the filling inlet in a simple and space-saving manner because there is no need for an illumination means from below. An inspection device is thus proposed in which the containers need not necessarily be transported "floor-free".

With devices according to the state of the art interruption of a floor-guided transport is normally required in order to illuminate the containers from below. Because there is then no need for such interruptions, potential savings can be achieved and also sources of error can be reduced.

With a preferred method an inspection of an empty container is carried out. Advantageously the container is a glass container and in particular a glass bottle. However it would be feasible to also apply the (possibly modified) method to plastic containers. Advantageously the containers to be inspected are in an opened state/as yet open.

The foreign bodies in particular are pieces of broken glass which may have inadvertently reached the inside of the container during the manufacturing process or in particular have reached its bottom. However, the foreign bodies could also be other foreign matter such as insects. Advantageously the tempered area and the inspected area lie opposite each other. As such the outside wall may be heated, in particular in the floor area of the container, and then the inside wall of this floor area may be inspected. Preferably therefore embodiments of the invention relates to the inspection of the floor of such containers.

Due to the proposed approach it is possible to detect foreign bodies such as pieces of broken glass or flies which may have fallen into the container, in particular just before filling takes place. To this end the container floor is preferably initially tempered and in particular heated and then the floor of the container is observed through the orifice of the container in order to detect foreign bodies based on different temperatures.

Another possibility would be to cool the container floor and in this way to detect foreign bodies which have fallen in from outside and which are warmer, due to the temperature difference.

In addition it would be possible to detect different emission values of materials of different density. As such it would for example be possible to introduce a drop of liquid nitrogen into the container, then wait for a short time, and then to take a picture through the container orifice in order to ascertain which areas have significantly cooled down.

Preferably the foreign bodies are therefore detected using a temperature difference between the foreign body and the container floor.

Preferably detection of heat radiation takes places after tempering/heating of the container has been completed. In this way it can be prevented that the measurements taken by the inspection device are themselves falsified by the heating means. With a further advantageous method heating of the containers is effected during transportation of the containers. As such it would be possible, for example, for the containers to be guided past a heating means which heats their bottom. Also a transport facility could itself be configured as a heating element or could encompass heating elements. As such a transport belt on which the containers are transported could, for example, encompass these heating elements, for example in the form of heated transport chain links.

With a further advantageous method inspection of the container is performed during transportation of the containers. Transportation may be continuous. But indexed transportation would also be possible, wherein the inspection means takes a picture during the standstill phase, respectively. Advantageously the inspection means comprises an imaging device which takes spatially-resolved pictures.

With a further advantageous method the containers are, at least in sections, supported in a floor area during their transportation. Advantageously the containers are transported on a transport belt, a transport chain or a transport disk and preferably also heated during this transport.

With a further advantageous method heating of the wall area of the container and in particular of a floor area is effected by a contact with a contact body. This contact body may for example be a heated transport belt.

In particular tempering/heating is effected by contact with the transport facility. Contactless heating would, however, also be possible, for example by application of a gaseous medium such as heated air.

Embodiments of the present invention are further directed at a device for inspecting containers, which device comprises a transport facility which transports the containers along a predefined transport path. Furthermore the device comprises a tempering means which at least tempers a wall area of the containers, and an inspection means arranged in a transport device of the containers downstream of the tempering device which inspects at least one section of the containers.

According to embodiments of the invention the inspection means comprises an imaging device for taking thermal images.

Therefore with regard to the device, it is proposed that the container sections, in particular the floor sections are initially heated by means of a heating means and then the heated (floor) area is observed by means of a thermal imaging camera in order to draw conclusions as regards any foreign bodies. Advantageously the tempering means is arranged in an area of the transport facility.

Advantageously the inspection means comprises an image-evaluating unit, which in particular detects areas of the image in which a different temperature occurs. Advantageously this evaluation means is configured such that it is able to differentiate between ordinary heat fluctuations and also between higher thermal image fluctuations which indicate the presence of foreign bodies.

As such it would be possible for a user to evaluate the recorded image, but it would also be possible for this evaluation to be effected electronically with a difference being recognised, from a defined temperature difference onwards, between the recorded floor area and individual sections thereof. With a further advantageous invention the device comprises an ejection/rejection means which ejects/rejects those containers in which foreign bodies are detected.

Advantageously the inspection means is arranged in a transport facility of the containers upstream of a filling means for filling these containers. Preferably the inspection means is arranged directly in front of a filling means. As such the filling means may comprise, for example, an infeed star-wheel which feeds the containers to the filling means, and the inspection means is preferably arranged in an area of this star-wheel. With regard to the method the containers and in particular their floors are preferably inspected directly prior to being filled (in particular with a beverage).

Advantageously the device comprises an indicating means, in particular an image output means or indicating means which records images output by the inspection means.

With a further advantageous embodiment the device comprises a filling means which is arranged downstream of the inspection means.

Advantageously the inspection means is an infrared camera which in particular records radiation in the infrared wavelength range.

With a further advantageous embodiment the tempering means is configured so as to be movable and in particular so as to move together with the containers. For example the tempering means may be configured in the form of transport chain links mentioned. It would, however, also be possible for the tempering means to be stationary and for the containers to move in relation to it.

With a further advantageous embodiment the transport facility performs a floor-supported transport of the containers. As such the transport facility may be configured as a transport belt, or a transport chain. The transport belt or chain links of the transport chain itself could be heatable and/or itself comprise openings through which the floor of the container is being acted upon by a heated medium or heated air. This heated air could be supplied from another section of the plant in which this air occurs as exhaust air.

With a further advantageous embodiment the transport means itself comprises the tempering means. Preferably the transport facility is a transport belt on which the containers are being conveyed (in particular standing upright).

With a further advantageous embodiment the inspection means is arranged to be stationary. Advantageously a further transport facility is provided for guiding the containers past this stationary inspection means. This further transport facility may be a transport star-wheel, past which the containers are guided for example with their outer circumference or their orifice area. Advantageously a movement of this further transport facility is synchronised with the inspection means, so that for example the synchronisation means causes images to be recorded when the inspection means is situated above the containers and can inspect the containers through their orifice.

However, provision may also be made for the transport belts to be joined together, wherein the heating means is arranged on the first transport belt and the inspection means is arranged on the second transport belt.

BRIEF DESCRIPTION

Figure 2:
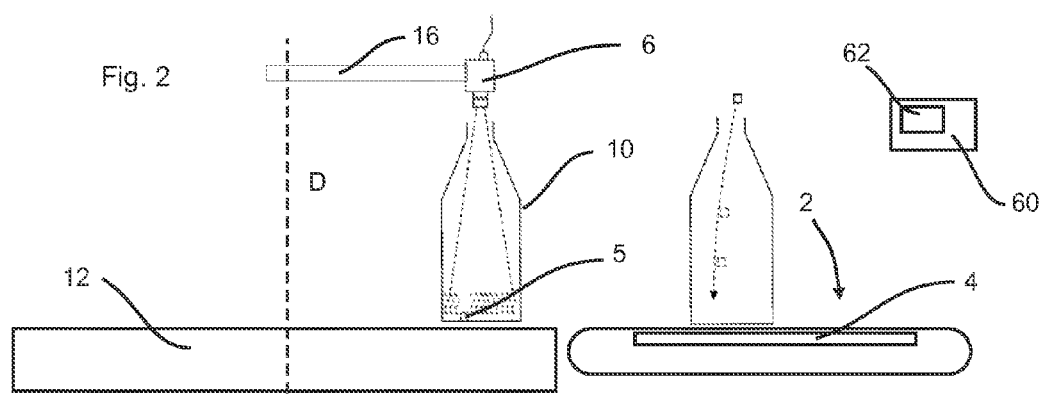
Figure 3:
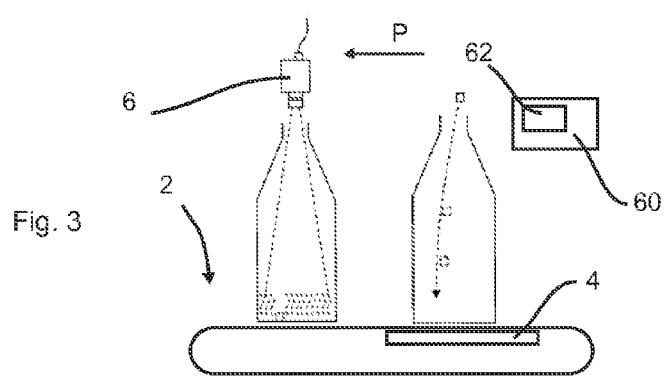

Some of the embodiments will be described in detail, with reference to the following figures, wherein like designations denote like members, wherein:

FIG. 1 shows a view of how the method is performed;
FIG. 2 shows a roughly schematic view of the device; and
FIG. 3 shows a further view of a device.

DETAILED DESCRIPTION

FIG. 1 shows a roughly schematic view in order to illustrate how the method according to embodiments of the invention is performed. A container 10 is shown which here is conveyed from right to left (arrow 1). In the right-hand view (I) this container 10 is heated by a heating means 4 arranged here below the container, in particular in a floor area 10a. Further, a foreign body 5 is schematically shown, which is in the process of just dropping into the container.

Next the container is transported further as illustrated by arrow P1 in order to be inspected (II). In this area the floor area 10a in particular emits heat radiation S. By contrast, no heat radiation is emitted in the area, in which the foreign body 5 lies, rather this is blocked.

Above the container 10 or above its orifice 10b, there is an inspection means or inspection device 6 such as in particular a thermal imaging camera, which observes the floor area 10a of the container 10 through the orifice 10b. To this end the inspection means 6 is focussed so as to record the floor area 10a. Advantageously the inspection means or the section of the inspection means 6 nearest the container is arranged at a distance from the rim of the orifice of the container 10, which is between 1 cm and 20 cm, preferably between 1 cm and 15 cm, preferably between 1 cm and 10 cm and especially preferably between 1 cm and 5 cm.

The inspection means 6 then records the outgoing heat radiation S, wherein however in the area in which the foreign body 5 lies, less or no heat radiation is emitted because this foreign body 5 was not heated or tempered in the same manner as the floor area 10a. In an image recorded by the inspection means 6, this area may for example be noticed as a dark stain.

FIG. 2 shows a roughly schematic view of a possible embodiment of the invention. Again, the transport facility 2 is shown, configured here, for example, as a circulating transport belt on which the container 10 is transported. Here the transport facility may have the heating means 4 integrated with it, which here is heating the floor area 10a of the container 10 by a contact with this floor area 10a.

Next the container 10 arrives at a second transport means 12 which here may be constructed as a rotating disk. The reference sign D denotes a rotary axis of this second transport means. In addition this second transport means 12 may comprise guiding elements which make contact with the outer circumference of the containers thereby guiding them (not shown). An inspection means 6 is arranged on a beam 16 in a stationary manner and positioned such that it is able to record images of the inside of the container 10 through the orifice thereof.

Based on an evaluation performed by an evaluation means 60, of images recorded by the inspection means 6 it is possible to ascertain as to whether foreign bodies are present in the container. To this end it is possible for a recorded image to be evaluated by means of the evaluation means and to be displayed, as required, on an indicating means 62.

Preferably image recording/inspection of the containers takes place immediately after heating is completed. Preferably a time span between the end of the heating phase and the inspection is smaller than 10 sec., preferably smaller than 5 sec., preferably smaller than 4 sec.

Preferably the inspection unit is arranged directly in front of a filling machine, especially preferably directly in front of the filling means, i.e. filler valve. With this arrangement the distance to the filler valve is less than 24 container divisions, preferably less than 12, preferably less than 6 divisions.

It is also possible for this evaluation means to compare recorded images with reference images in order to determine as to whether foreign bodies are present in the container. If one assumes, for example, a case in which embodiments of the invention is applied to glass containers, a simplified transmission spectrum of glass may be used as a basis. This comprises a significant decrease in transmission in a range from 2.8 µm 4.5 µm. In empty container inspection an inspection means/infrared camera which is operative in a range of 3.5 µm, will yield good inspection results when pieces of broken glass are detected. In this way even dark-field inspections which yield unsatisfactory recognition results can be replaced by the method according to embodiments of the invention. Preferably the inspection means comprises a recognisable wavelength range which is larger than 1000 nm, preferably larger than 2000 nm.

The inspection unit is preferably operative in an infrared wavelength range, in which glass is almost impermeable to (IR) light such that the heated container floor serves as a luminous area and no interferences are caused by the background. The unit shall thus be operated in a wavelength range >2.8 mm, preferably >4 µm and especially preferably >5 µm. In order to minimise external radiation, a band-pass filter may preferably be used. This band-pass filter preferably allows wavelengths to pass which are below 1000 µm, preferably below 100 µm and especially preferably below 50 µm. Advantageously a semiconductor material is used as detector material for the inspection means, in particular a material which is selected from a group of materials containing InGaAs, InSb, InAsSb, PbS, PbSe, Poly-SiGe, Bi/Sb, combinations thereof etc. It is also possible to use photon detectors as well as bolometers or thermopiles. Furthermore it is possible to cool the container side wall in order to minimise IR external radiation and to increase contrast in the floor area.

Preferably an evaluation unit for evaluating the recorded images, for example a corresponding chip, has an integration time which is less than 2 ms, preferably less than 1 ms and especially preferably less than 500 µs. The transport speeds of a corresponding device for the treatment of containers are preferably higher than 10,000 containers/h, preferably higher than 20,000 containers/h and especially preferably higher than 40,000 containers/h.

FIG. 3 shows a further embodiment of the present invention. With this embodiment both heating of the floor area and inspection using the inspection means 6 take place during transport with such the transport facility. To this end the heating means 4 is arranged in an initial area (viewed in transport direction P of the containers) of the transport facility 2. Preferably the heating means 4 is arranged here in a stationary manner. The inspection means is arranged in a second section of the transport facility 2. Here inspection of the containers can be performed directly after they have been heated tempered.

The applicant reserves the right to claim all of the features disclosed in the application documentation, individually or in combination, as being essential to embodiments of the invention, in case these are new relative to the state of the art, individually or in combination.

LIST OF REFERENCE SIGNS 1 device
2 transport facility
4 tempering means
5 foreign body
6 inspection means
10 container
10a floor area of the container 10
10b orifice of the container 10
12 further transport means
16 beam
60 evaluation means
62 indicating means
P1 direction of transportation
S heat radiation
D rotary axis Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method for inspecting drink containers, transporting a drink container along a predefined transport path by means of a transport facility, tempering an outside wall of the container at least in sections, and inspecting an area of the inside wall of the container through an orifice of the container during or after tempering of the outside wall by means of an inspection means,
   detecting with the inspection means heat radiation emanating from the observed area of the inside wall and concluding from the detected heat radiation as to the presence of foreign bodies between the observed area of the inside wall and the inspection means;
   wherein the inspection means is operated in a wavelength range above 5 µm.

2. The method according to claim 1, wherein heat radiation is detected after heating of the container has been completed.

3. The method according to claim 2, wherein the inspection of the area of the inside wall of the container through an orifice of the container after tempering of the outside wall.

4. The method according to claim 1, wherein heating of the container is carried out during transportation of the container.

5. The method according to claim 1, wherein inspection of the container by the inspection means is carried out during transportation of the container.

6. The method according to claim 1, wherein the containers, at least in sections, are supported in a floor area during transportation.

7. The method according to claim 1, wherein heating of the wall area is effected through contact with a contact body.

8. A device for inspecting containers with a transport facility which transports the containers along a predefined transport path, with a tempering means which tempers at least one wall area of the container, and an inspection device arranged in transport direction of the container downstream relative of the tempering means, which inspects at least one section of the containers,
   wherein the inspection device comprises an image recording means recording thermal images, and the inspection means is operated in a wavelength range above 5 µm.

9. The device according to claim 8, wherein the tempering means is configured so as to move together with the containers.

10. The device according to claim 8, wherein the transport facility comprises the tempering means.

11. The device according to claim 8, wherein the inspection device is arranged so as to be stationary.

12. The device according to claim 8, wherein the inspection device is arranged in a transport direction of the containers directly in front of a filling means for filling the containers.

13. The device according to claim 8, wherein the tempering means tempers at least one outside wall of the container, and the inspection device inspects at least one section of the inside wall of the container.

14. The device according to claim 8, wherein the device is suitable for inspecting containers out of glass, and wherein the inspection device is operative in an infrared wavelength range, in which glass is almost impermeable to infrared light.

15. The device according to claim 8, wherein the container side wall is cooled.

16. The device according to claim 8, wherein the device comprises a filling means which is arranged directly downstream of the inspection means.

17. The method according to claim 1 for inspecting drinks containers out of glass, wherein the inspection method is operative in an infrared wavelength range, in which glass is almost impermeable to infrared light.

18. The method according to claim 1, comprising cooling the container side wall in order to minimize IR external radiation and to increase contrast in the floor area.

19. The method according to claim 1, comprising inspecting the floors of the containers directly prior to being filled.

* * * * *